United States Patent
Nagl et al.

(10) Patent No.: US 9,615,181 B2
(45) Date of Patent: Apr. 4, 2017

(54) SYMMETRIC MAGNET ARRANGEMENT FOR MEDICAL IMPLANTS

(71) Applicant: Vibrant Med-El Hearing Technology GmbH, Innsbruck (AT)

(72) Inventors: Markus Nagl, Volders (AT); Thomas Lechleitner, Polling (AT); Peter Lampacher, Innsbruck (AT); Wolfgang Amrhein, Ottensheim (AT); Gunther Weidenholzer, Ottensheim (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 398 days.

(21) Appl. No.: 13/937,442

(22) Filed: Jul. 9, 2013

(65) Prior Publication Data
US 2014/0012071 A1 Jan. 9, 2014

Related U.S. Application Data

(60) Provisional application No. 61/669,161, filed on Jul. 9, 2012.

(51) Int. Cl.
*H04R 25/00* (2006.01)
*A61N 1/375* (2006.01)
(Continued)

(52) U.S. Cl.
CPC ............... *H04R 25/60* (2013.01); *A61N 1/08* (2013.01); *A61N 1/36032* (2013.01);
(Continued)

(58) Field of Classification Search
CPC ........ H04R 25/00; H04R 25/60; A61N 1/375; A61N 1/36032; A61N 1/3718; A61N 1/08
(Continued)

(56) References Cited

U.S. PATENT DOCUMENTS

| | | | |
|---|---|---|---|
| 3,487,403 A | 12/1969 | Pihl | 340/373 |
| 3,573,812 A | 4/1971 | Pihl | 340/373 |

(Continued)

FOREIGN PATENT DOCUMENTS

| | | | |
|---|---|---|---|
| EP | 2031896 | 4/2009 | ............ H04R 25/00 |
| GB | 1468890 | 3/1977 | |

(Continued)

OTHER PUBLICATIONS

Bromberg & Sunstein LLP, Response A filed May 14, 2007 to Office Action dated Feb. 12, 2007, pertaining to U.S. Appl. No. 11/158,322, 14 pages.

(Continued)

*Primary Examiner* — Navin Natnithithadha
*Assistant Examiner* — Sunita Reddy
(74) *Attorney, Agent, or Firm* — Sunstein Kann Murphy & Timbers LLP

(57) ABSTRACT

An arrangement is described for a hearing implant system. An implantable housing has an outer surface configured to lie under and parallel to the skin of the implanted patient. An implant magnet arrangement is located within the implantable housing and has multiple local magnetic sections with different independent local magnetic fields that are combined together to form a net magnetic field with at least two-fold symmetry and zero net magnetic dipole moment, wherein the magnetic fields are oriented parallel to the outer surface of the implant housing.

1 Claim, 6 Drawing Sheets

(51) Int. Cl.
    *A61N 1/08*     (2006.01)
    *A61N 1/36*     (2006.01)
    *A61N 1/37*     (2006.01)

(52) U.S. Cl.
    CPC ............ *A61N 1/375* (2013.01); *H04R 25/00* (2013.01); *H04R 25/556* (2013.01); *H04R 25/606* (2013.01); *A61N 1/3718* (2013.01)

(58) Field of Classification Search
    USPC ......... 600/25; 607/136, 137; 623/10; 381/60
    See application file for complete search history.

(56) References Cited

U.S. PATENT DOCUMENTS

| | | | |
|---|---|---|---|
| 3,801,767 A | 4/1974 | Marks | 200/161 |
| 3,987,967 A | 10/1976 | Kuznetsov et al. | 241/1 |
| 4,038,990 A | 8/1977 | Thompson | 128/419 PG |
| 4,199,741 A | 4/1980 | Serrus Paulet | 335/206 |
| 4,257,936 A | 3/1981 | Matsumoto et al. | 524/413 |
| 4,317,969 A | 3/1982 | Riegler et al. | 200/52 R |
| 4,549,532 A | 10/1985 | Baermann | 600/15 |
| 4,596,971 A | 6/1986 | Hirabayashi et al. | 335/205 |
| 4,628,907 A | 12/1986 | Epley | 128/1.6 |
| 4,785,816 A | 11/1988 | Dow et al. | 128/660 |
| RE32,947 E | 6/1989 | Dormer et al. | 128/420.6 |
| 4,868,530 A | 9/1989 | Ahs | 335/207 |
| 4,918,745 A | 4/1990 | Hutchison | 455/41 |
| 5,015,224 A | 5/1991 | Maniglia | 600/25 |
| 5,183,056 A | 2/1993 | Dalen et al. | 128/782 |
| 5,434,549 A | 7/1995 | Hirabayashi et al. | 335/229 |
| 5,456,654 A | 10/1995 | Ball | 600/25 |
| 5,538,219 A | 7/1996 | Osterbrink | 251/129.15 |
| 5,554,096 A | 9/1996 | Ball | 600/25 |
| 5,624,376 A | 4/1997 | Ball et al. | 600/25 |
| 5,630,835 A | 5/1997 | Brownlee | 607/60 |
| 5,716,407 A | 2/1998 | Knapp et al. | 623/11 |
| 5,724,014 A | 3/1998 | Leikus et al. | 335/4 |
| 5,749,912 A | 5/1998 | Zhang et al. | 607/57 |
| 5,800,336 A | 9/1998 | Ball et al. | 600/25 |
| 5,857,958 A | 1/1999 | Ball et al. | 600/25 |
| 5,877,664 A | 3/1999 | Jackson, Jr. | 335/205 |
| 5,897,486 A | 4/1999 | Ball et al. | 600/25 |
| 5,913,815 A | 6/1999 | Ball et al. | 600/25 |
| 6,040,762 A | 3/2000 | Tompkins | 340/426 |
| 6,067,474 A | 5/2000 | Schulman et al. | 607/57 |
| 6,175,767 B1 | 1/2001 | Doyle, Sr. | 607/57 |
| 6,178,079 B1 | 1/2001 | Renger | 361/118 |
| 6,178,353 B1 | 1/2001 | Griffith et al. | 607/61 |
| 6,190,305 B1 | 2/2001 | Ball et al. | 600/25 |
| 6,208,235 B1 | 3/2001 | Trontelj | 340/10.1 |
| 6,208,882 B1 | 3/2001 | Lenarz et al. | 600/379 |
| 6,217,508 B1 | 4/2001 | Ball et al. | 600/25 |
| 6,219,580 B1 | 4/2001 | Faltys et al. | 607/57 |
| 6,292,678 B1 | 9/2001 | Hall et al. | 600/274 |
| 6,295,472 B1 | 9/2001 | Rubinstein et al. | 607/55 |
| 6,313,551 B1 | 11/2001 | Hazelton | 310/12 |
| 6,348,070 B1 | 2/2002 | Teissl et al. | 623/11.11 |
| 6,358,281 B1 | 3/2002 | Berrang et al. | 623/10 |
| 6,475,134 B1 | 11/2002 | Ball et al. | 600/25 |
| 6,505,062 B1 | 1/2003 | Ritter et al. | 600/407 |
| 6,506,987 B1 | 1/2003 | Woods | 290/61.62 |
| 6,522,909 B1 | 2/2003 | Garibaldi et al. | 600/424 |
| 6,838,963 B2 | 1/2005 | Zimmerling et al. | 335/205 |
| 7,091,806 B2 | 8/2006 | Zimmerling et al. | 335/207 |
| 7,190,247 B2 | 3/2007 | Zimmerling | 335/205 |
| 7,266,209 B1 | 9/2007 | House | 381/331 |
| 7,338,035 B2 | 3/2008 | Tsai | 267/136 |
| 7,566,296 B2 | 7/2009 | Zimmerling et al. | 600/25 |
| 7,608,035 B2 | 10/2009 | Farone | 600/9 |
| 7,642,887 B2 | 1/2010 | Zimmerling | 335/296 |
| 2002/0066702 A1* | 6/2002 | Liu | A61N 2/00 210/695 |
| 2004/0012470 A1 | 1/2004 | Zimmerling et al. | 335/207 |
| 2005/0001703 A1 | 1/2005 | Zimmerling | 335/220 |
| 2005/0062567 A1 | 3/2005 | Zimmerling et al. | 335/150 |
| 2006/0244560 A1 | 11/2006 | Zimmerling et al. | 335/207 |
| 2007/0100197 A1* | 5/2007 | Perkins | H04R 23/008 600/25 |
| 2007/0191673 A1 | 8/2007 | Ball et al. | 600/25 |
| 2007/0274551 A1 | 11/2007 | Tsai et al. | 381/326 |
| 2009/0209806 A1 | 8/2009 | Hakansson | 600/25 |
| 2010/0004716 A1 | 1/2010 | Zimmerling et al. | 607/57 |
| 2010/0145135 A1 | 6/2010 | Ball et al. | 600/25 |
| 2010/0324355 A1 | 12/2010 | Spitaels et al. | 600/25 |
| 2011/0022120 A1 | 1/2011 | Ball et al. | 607/57 |
| 2011/0216927 A1 | 9/2011 | Ball | 381/313 |
| 2011/0264172 A1* | 10/2011 | Zimmerling | A61N 1/36032 607/60 |
| 2012/0029267 A1 | 2/2012 | Ball | 600/25 |
| 2012/0296155 A1* | 11/2012 | Ball | A61N 1/36032 600/25 |
| 2013/0002382 A1* | 1/2013 | Zhang | H01F 7/0221 335/285 |

FOREIGN PATENT DOCUMENTS

| | | | | |
|---|---|---|---|---|
| JP | 04/023821 | 1/2004 | ............ | H04R 25/00 |
| SU | 1690749 | 11/1991 | ............ | A61F 11/04 |
| WO | WO 97/032629 | 9/1997 | ............ | A61N 1/32 |
| WO | WO 00/10361 | 2/2000 | | |
| WO | WO 03/036560 A2 | 5/2003 | ............ | G06K 11/18 |
| WO | WO 03/081976 A2 | 10/2003 | | |
| WO | WO 03/092326 A1 | 11/2003 | ............ | H04R 25/00 |
| WO | WO 2004/114723 | 12/2004 | ............ | H04R 25/00 |
| WO | WO 2011/011409 | 1/2011 | ............ | A61N 1/136 |
| WO | WO 2011/133747 | 10/2011 | ............ | A61N 1/36 |

OTHER PUBLICATIONS

Bromberg & Sunstein LLP, Response B filed Jun. 17, 2008 to Office Action dated Mar. 17, 2008, pertaining to U.S. Appl. No. 11/158,322, 10 pages.

Bromberg & Sunstein LLP, Response C filed Sep. 19, 2008 to Office Action dated Jun. 26, 2008, pertaining to U.S. Appl. No. 11/671,132, 8 pages.

Bromberg & Sunstein LLP, Response D filed Jan. 5, 2009 to Office Action dated Oct. 27, 2008, pertaining to U.S. Appl. No. 11/671,132, 13 pages.

European Patent Office, European Search Report (Extended) pertaining to Application No. 08075886.5-2205/12031896, date of mailing Jun. 3, 2009, 8 pages.

Heller et al, "Evaluation of MRI Compatibility of the Modified Nucleus Multichannel Auditory Brainstem and Cochlear Implants", *The American J. Of Otology* 17(5); pp. 724-729 (Sep. 1996).

Hobbs, et al, "Magnetic Resonance Image—Guided Proteomics of Human Glioblastoma Multiforme", *Journal of Magnetic Resonance Imaging*; pp. 530-536 (2003).

International Searching Authority, International Search Report International Application No. PCT/IB03/02283, date of mailing Nov. 28, 2003, 7 pages.

International Searching Authority, Invitation to Pay Additional Fees—International Application No. PCT/IB2004/002588, date of mailing Dec. 20, 2004, 4 pages.

Teissl et al, "Cochlear Implants: In Vitro Investigation of Electromagnetic Interference at MR Imaging—Compatibility and Safety Aspects", *Radiology* 208(3); pp. 700-708 (Sep. 1998).

Teissl et al, "Magnetic Resonance Imaging and Cochlear Implants: Compatibility and Safety Aspects", *J. Magn. Reson. Imaging* 9(1); pp. 26-38 (Jan. 1999).

United States Patent and Trademark Office, Office Action dated Feb. 12, 2007, pertaining to U.S. Appl. No. 11/158,322, 6 pages.

United States Patent and Trademark Office, Office Action dated Mar. 17, 2008, pertaining to U.S. Appl. No. 11/158,322, 14 pages.

United States Patent and Trademark Office, Office Action dated Oct. 27, 2008, pertaining to U.S. Appl. No. 11/671,132, 7 pages.

International Searching Authority, Authorized Officer Lee W. Young, International Search Report and Written Opinion, PCT/US11/41045, mailed Oct. 25, 2011, 10 pages.

(56) References Cited

OTHER PUBLICATIONS

International Searching Authority, Authorized Officer Shane Thomas, International Search Report and Written Opinion, PCT/US12/70823, date of mailing Mar. 13, 2013, 13 pages.
International Searching Authority, Authorized Office Shane Thomas, International Search Report and Written Opinion, PCT/US13/28183, date of mailing May 10, 2013, 13 pages.
International Searching Authority, Authorized Officer Frank Liebmann, International Search Report and Written Opinion, PCT/US2013/049642, date of mailing Jan. 8, 2014, 11 pages.

\* cited by examiner

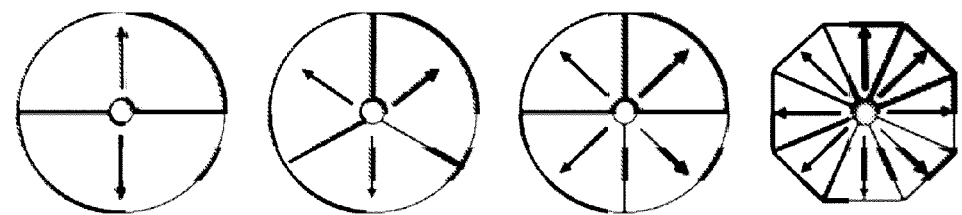
Fig. 5
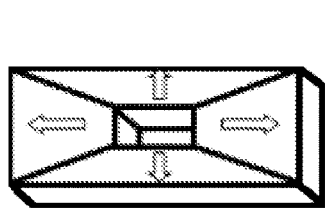 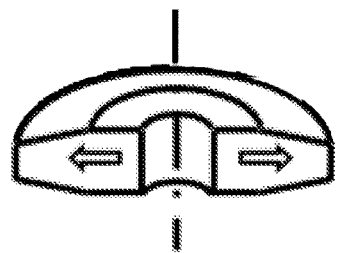 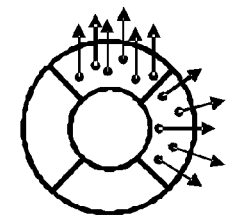
Fig. 6A　　　　Fig. 6B　　　　Fig. 6C

SYMMETRIC MAGNET ARRANGEMENT FOR MEDICAL IMPLANTS

This application claims priority from U.S. Provisional Patent Application 61/669,161, filed Jul. 9, 2012, which is incorporated herein by reference in its entirety.

FIELD OF THE INVENTION

The present invention relates to medical implants, and more specifically to a permanent magnet arrangement for use in such implants.

BACKGROUND ART

Some hearing implants such as Middle Ear Implants (MEI's) and Cochlear Implants (CI's) employ attachment magnets in the implantable part and an external part to hold the external part magnetically in place over the implant. For example, as shown in FIG. 1, a typical cochlear implant system may include an external transmitter housing 101 containing transmitting coils 107 and an external magnet 105. The external magnet 105 has a conventional coin-shape and a north-south magnetic dipole that is perpendicular to the skin of the patient to produce external magnetic field lines $M_1$ as shown. Implanted under the patient's skin is a corresponding receiver assembly 102 having similar receiving coils 108 and an implanted internal magnet 106. The internal magnet 106 also has a coin-shape and a north-south magnetic dipole that is perpendicular to the skin of the patient to produce internal magnetic field lines $M_2$ as shown. The internal receiver housing 102 is surgically implanted and fixed in place within the patient's body. The external transmitter housing 101 is placed in proper position over the skin covering the internal receiver assembly 102 and held in place by interaction between the internal magnetic field lines $M_2$ and the external magnetic field lines $M_1$. Rf signals from the transmitter coils 107 couple data and/or power to the receiving coil 108 which is in communication with an implanted processor module (not shown).

One problem arises when the patient undergoes Magnetic Resonance Imaging (MRI) examination. Interactions occur between the implant magnet and the applied external magnetic field for the MRI. As shown in FIG. 2, the direction of magnetization $\vec{m}$ of the implant magnet 202 is essentially perpendicular to the skin of the patient. Thus, the external magnetic field $\vec{B}$ from the MRI may create a torque $\vec{T}$ on the internal magnet 202, which may displace the internal magnet 202 or the whole implant housing 201 out of proper position. Among other things, this may damage the adjacent tissue in the patient. In addition, the external magnetic field $\vec{B}$ from the MRI may reduce or remove the magnetization $\vec{m}$ of the implant magnet 202 so that it may no longer be strong enough to hold the external transmitter housing in proper position. The implant magnet 202 may also cause imaging artifacts in the MRI image, there may be induced voltages in the receiving coil, and hearing artifacts due to the interaction of the external magnetic field $\vec{B}$ of the MRI with the implanted device. This is especially an issue with MRI field strengths exceeding 1.5 Tesla.

Thus, for existing implant systems with magnet arrangements, it is common to either not permit MRI or at most limit use of MRI to lower field strengths. Other existing solutions include use of surgically removable magnets, spherical implant magnets (e.g. U.S. Pat. No. 7,566,296), and various ring magnet designs (e.g., U.S. Patent Publication 20110022120), all of which are incorporated herein by reference. Among those solutions that do not require surgery to remove the magnet, the spherical magnet design may be the most convenient and safest option for MRI removal even at very high field strengths. But the spherical magnet arrangement requires a relatively large magnet much larger than the thickness of the other components of the implant, thereby increasing the volume occupied by the implant. This in turn can create its own problems. For example, some systems, such as cochlear implants, are implanted between the skin and underlying bone. The "spherical bump" of the magnet housing therefore requires preparing a recess into the underlying bone. This is an additional step during implantation in such applications which can be very challenging or even impossible in case of very young children.

Various complicated arrangements of magnetic elements have been described for use in hearing implant applications. See for example, U.S. Pat. No. 4,549,532; U.S. Pat. No. 7,608,035; U.S. Patent Publication 20110022120; and U.S. Patent Publication 20110264172, which are incorporated herein by reference. However, there is no suggestion that such therapeutic arrangements might potentially have any utility for magnetic attachment applications such as those described above.

SUMMARY OF THE INVENTION

Embodiments of the present invention are directed to an arrangement for a medical implant system. An implantable housing has an outer surface configured to lie under and parallel to the skin of the implanted patient. An implant magnet arrangement is located within the implantable housing and has multiple local magnetic sections with different independent local magnetic fields that are combined together to form a net magnetic field with at least two-fold symmetry (e.g., radial symmetry) and zero net magnetic dipole moment, wherein the magnetic fields are oriented parallel to the outer surface of the implant housing.

The implant magnet arrangement may have an inner local magnetic section having a first local magnetic field and an outer circumference local magnetic section having a second local magnetic field, wherein the first local magnetic field and the second local magnetic field have different directional orientations; for example, the implant magnet arrangement may be disk shaped. There may be at least one local magnetic field with a directional orientation emanating from a common radial center and/or a directional orientation with substantially parallel magnetic field lines.

The implant magnet arrangement may function as a holding magnet to magnetically interact with an external magnet arrangement in an external device to hold the external device in a fixed position on the skin of the patient user. Or the implant magnet arrangement may function as an actuator magnet in an implantable transducer to generate a mechanical vibration signal in the patient user.

Embodiments of the present invention also are directed to an implantable transducer arrangement for a medical implant system for a patient user. An implantable housing has an outer surface configured to lie under and parallel to the skin of the implanted patient. A magnetic transducer is located within the implantable housing and is adapted to magnetically interact with an external magnetic drive component on the skin of the patient user to develop a mechanical stimulation signal to the implantable housing. The magnetic transducer includes a transducer magnet arrangement having multiple local magnetic sections with different independent local magnetic fields that are combined together to form a net magnetic field with at least two-fold symmetry (e.g., radial symmetry) and zero net magnetic dipole moment, wherein the magnetic fields are oriented parallel to the outer surface of the implant housing In further such embodiments, the transducer magnet arrangement includes an inner local magnetic section having a first local magnetic field and an outer circumference local magnetic section having a second local magnetic field, wherein the first local magnetic field and the second local magnetic field have different directional orientations. The transducer magnet arrangement may have a disk shape. At least one local magnetic field may have a directional orientation emanating from a common radial center and/or a directional orientation with substantially parallel magnetic field lines.

There may also be one or more suspension elements that are resiliently attached to the transducer magnet arrangement so that the magnetic transducer forms a coupled oscillating system with the external magnetic drive component. For example, the transducer magnet arrangement may include an inner local magnet and an outer circumference local magnet, wherein the one or more suspension elements resiliently connect the local magnets to each other.

In any of the above, the medical implant system may be a hearing implant system such as a cochlear implant system, a middle ear implant system, a bone conduction hearing implant system, or a vestibular implant system.

BRIEF DESCRIPTION OF THE DRAWINGS

FIG. 5 shows various alternative embodiments having multiple separate magnetic segments.

FIG. 6A-C shows various embodiments of implantable magnet arrangements having multiple separate magnetic segments with two-fold symmetry.

DETAILED DESCRIPTION OF SPECIFIC EMBODIMENTS

Various embodiments of the present invention are directed to a two-fold symmetric implant magnet arrangement (e.g., radially symmetric) for a medical implant system including without limitation hearing implants (cochlear implant, middle ear implant, bone conduction implant, or vestibular implant), visual implants and laryngeal pacemakers. The magnet arrangement produces a low torque in the presence of an external homogenous magnetic field such as for an MRI examination, yet the near field magnetic force (for magnetic interaction with a corresponding external holding magnet) is high enough to be comparable to that produced by a conventional cylindrical magnet. Such magnet arrangements can be useful both for functioning as a holding magnet component to hold an external unit in a desired position on the skin of the patient user, and also for functioning as an actuator magnet in a mechanical stimulation implant such as a bone conduction implant.

Figure 3A:
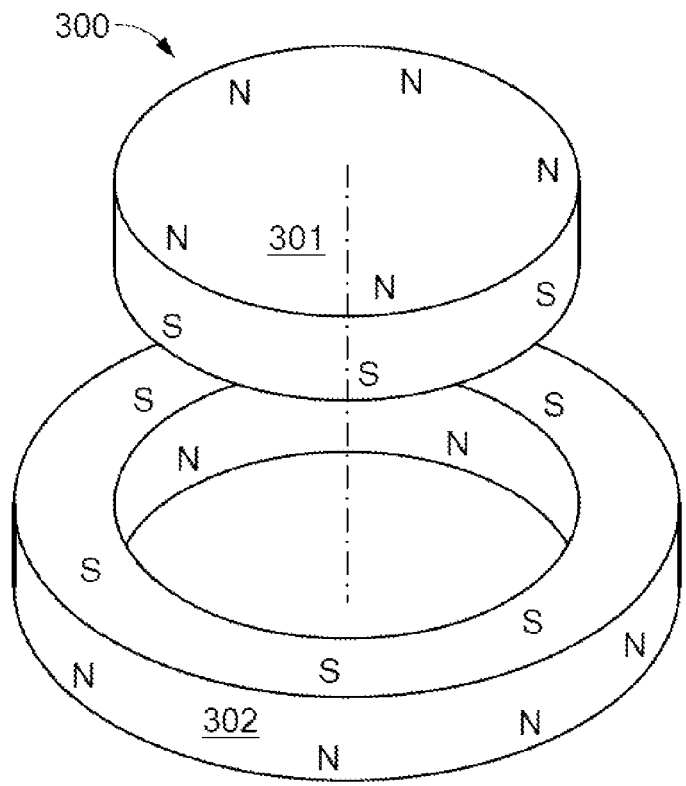
FIG. 3A-B shows an implant magnet arrangement with multiple magnetic field orientations.
Figure 3B:
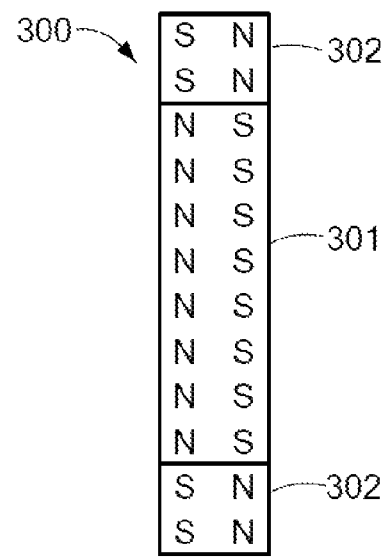

FIG. 3A shows an exploded elevated view and FIG. 3B shows a side view of an implant magnet arrangement 300 included in an implantable housing (e.g., implant housing 102) containing a portion of an implantable electronic system. A cylindrical implant magnet arrangement 300 within the housing includes an inner center disc section 301 having an inner magnetic orientation in an inner magnetic direction, and an outer radial ring section 302 having an outer magnetic orientation in an outer magnetic direction opposite to the inner magnetic direction. With such an arrangement, the net magnetic field of the implant magnet arrangement 300 is much less than in the conventional cylindrical magnet of the prior art, while locally the magnetic fields are still effectively strong near the inner center disc section 301 and the outer radial ring section 302 so that there is no overall loss in the retention force of the implant magnet arrangement 300. Such a reduced net magnetic field of the implant magnet arrangement 300 also avoids the prior problems of the net magnetic fields adversely interacting with the implant signal coil and its communications signal and reduces the torque and imaging problems of the prior art with regards to MRI procedures. Moreover, the greater specificity of the magnetic structures of the implant magnet arrangement 300 compared with a simple disk magnet also provides improved centering capability with regards to the external component housing.

Figure 1:
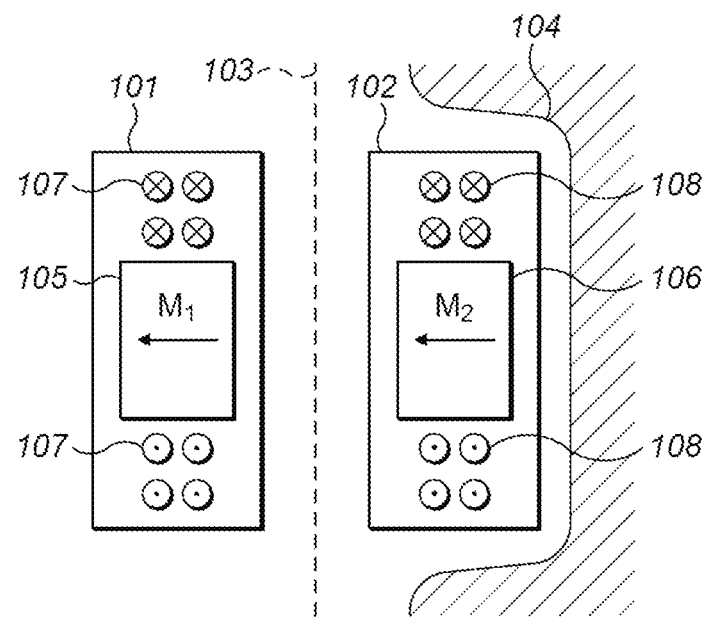
FIG. 1 shows a portion of a typical idealized cochlear implant which may be used in embodiments of the present invention.
Figure 2:
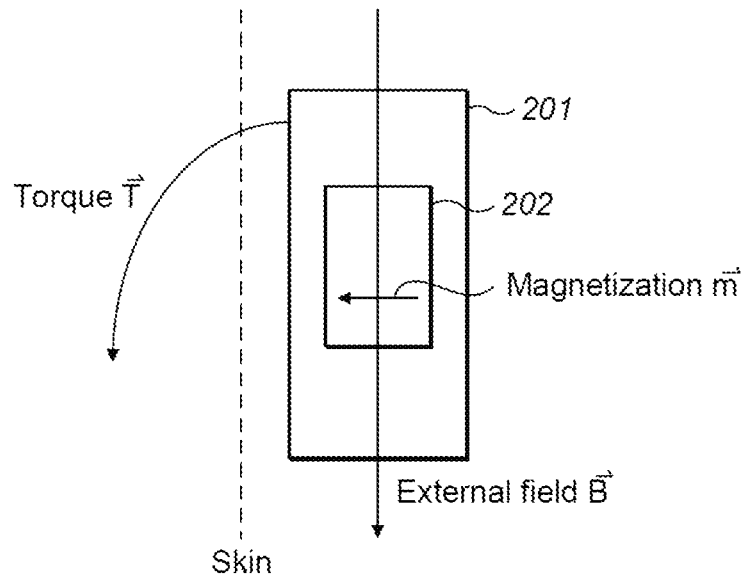
FIG. 2 shows effects of an external magnetic field on an implanted portion of an implanted device which may be used in embodiments of the present invention.
Figure 4A:
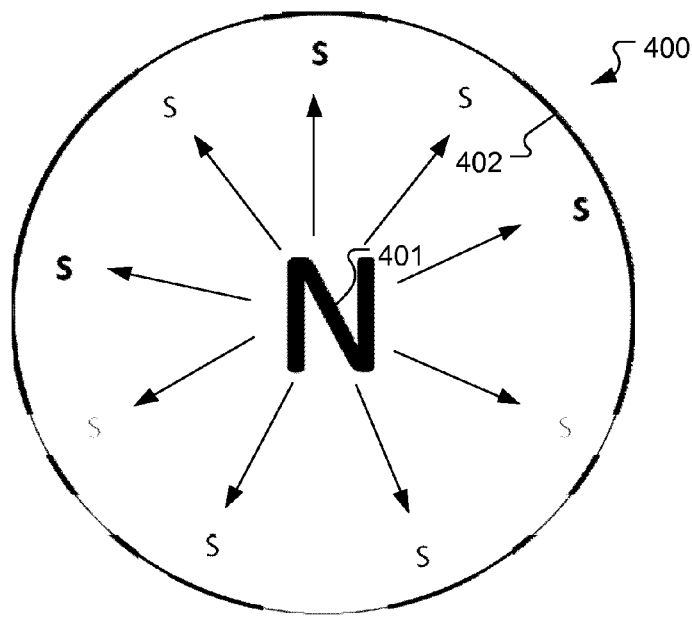
FIG. 4A-B shows a symmetric implant magnet according to an embodiment of the present invention.

FIG. 4A shows a top plan view of an implant magnet 400 with at least two-fold symmetry for a hearing implant system according to an embodiment of the present invention. The implant magnet 400 here has a conventional disk shape with radial symmetry that fits normally inside an implantable housing of the type used in a hearing implant system that has an outer surface configured to lie under and parallel to the skin of the implanted patient (e.g., implant housing 102 in FIG. 1). The implant magnet 400 has an inner local magnetic section 401 at its radial center where a first local magnetic field is located (here, the North pole), and an outer circumference local magnetic section 402 around which a second local magnetic field is distributed (here the South pole). This radially symmetric implant magnet 400 as shown in FIG. 4A has a net magnetic field that is parallel to the outer housing surface and a net magnetic dipole moment near zero. The magnetic flux at the radial center 401 of the implant magnet 400 would still be comparable to that in a conventional disk shaped implant magnet.

Figure 4B:
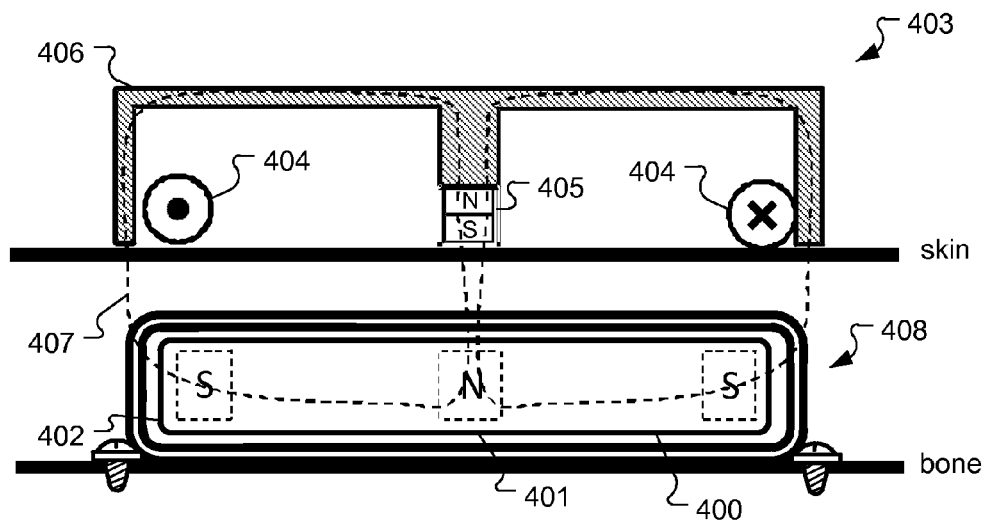

The implant magnet 400 may function as an actuator magnet in an implantable transducer to generate a mechanical vibration signal in the patient user. FIG. 4B shows a side cross-section of such an actuator implant magnet 400 within a transducer housing 408 that is implanted under the skin of a patient user to magnetically interact with an external magnet arrangement 405 in an external device 403 to hold it in a fixed position on the skin. Here the external magnet arrangement 405 is a conventionally vertically magnetized cylinder which cooperates with the radially magnetized implant magnet 400 by means of a magnetic yoke 406 of ferromagnetic material that directs the magnetic fields 407 as shown between the external magnet arrangement 405 and the implant magnet 400 so that the magnetic fields pass vertically through the external magnet arrangement 405 and horizontally through the implant magnet 400. To that end the magnetic yoke 406 should be about the same size or slighter larger in diameter than the implant magnet 400.

Typically, the external device 403 would include a transmitter driving coil 404 for transmitting a communications signal through the skin. The external device 403 senses environmental sound (via a microphone—not shown) and converts the acoustic information to an electromagnetic driving signal through the skin to the implant magnet 401 that responsively vibrates. The transducer housing 408 couples the vibration to the skull bone and by bone conduction to the fluid within the cochlea where it is perceived as sound. As compared to the implant magnet arrangement 300 in FIG. 3A-B, the radially symmetric implant magnet 400 in FIGS. 4A-B has a more compact magnetic field which favorably increases the magnetic coupling efficiency, thereby leading to superior holding and vibration characteristics. As an alternative to a permanent magnet, the external device 403 may instead contain a ferromagnetic material such as iron, nickel, cobalt, etc. that magnetically interacts with the implant magnet 400.

A two-fold symmetric implant magnet may be a single piece radially symmetric magnet as shown in FIG. 4A, or embodiments may having multiple separate magnetic segments: 2, 3, 4, 6, 8, etc. as shown in FIG. 5. Such implant magnets would still need to have a net magnetic dipole moment of near zero, i.e., the sum of the individual magnetic dipole moments would be near zero. The individual segments would have less issues arising from undesired eddy current losses than might be the case in a single piece implant magnet design. An implant magnet composed of multiple magnet segments as in FIG. 5 also may be less susceptible to problems with manufacturing tolerances since the magnet segments can advantageously self-adjust to a symmetric configuration within the implant housing.

The implant magnet also may have any convenient specific shape with at least two-fold symmetry in the sense that the shape looks the same after a 180-degree rotation. That is the implant magnet may have radial symmetry as with a circular disk, an annular ring disk with a center hole, or a polygonal disk shape. Such shapes may be either freely rotatable about the radial center or non-rotatably fixed within the implantable housing. Or the implant magnet may not have radial symmetry as such, but still have at least two-fold symmetry as in the embodiments shown in FIG. 6A-C. FIG. 6A shows an implant magnet made of multiple separate magnetic segments that form a rectangular shape. FIG. 6B shows multiple magnetic segments that form a half-ring shape with two fold symmetry. FIG. 6C shows another variation where multiple magnetic segments form a ring-shape implant magnet wherein the segments alternate with every other segment having either a local magnetic field with a directional orientation emanating from a common radial center or a directional orientation with substantially parallel magnetic field lines.

Figure 7A:
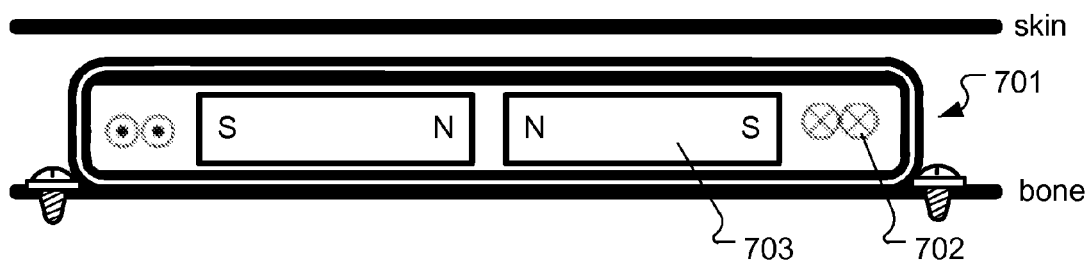
FIG. 7A-B shows various relationships between an implant magnet arrangement and the receiving coil in the implant housing.
Figure 7B:
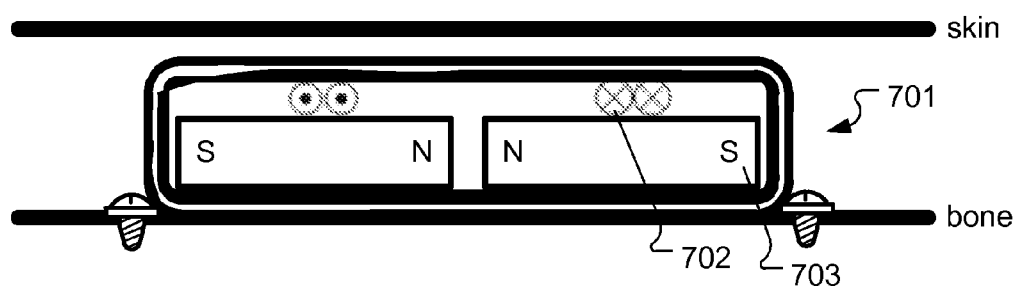

In a typical hearing implant system application, the implant magnet may be in an implantable housing with additional functional elements such as a receiving coil for transcutaneously receiving an implant communication signal from an external transmitter device fixedly attached on the skin of the implant patient by the holding force of an external magnet arrangement adapted for magnetic interaction with the implant magnet. FIG. 7A-B shows various relationships between an implant magnet arrangement 703 that functions as a holding magnet and the receiving coil 702 in the implant housing 701. The implant housing 701 has a planar outer surface that lies parallel to the overlying skin and the receiver coil 702 within the implant housing 701 lies parallel to the planar outer surface (i.e., parallel to the skin) and can be either outside the outer circumference of the implant magnet arrangement 703 as shown in FIG. 7A (the typical arrangement in a hearing implant system), or within the outer circumference of the implant magnet arrangement 703 as shown in FIG. 7B. The external magnet arrangement in the external device (not shown) may have the same shape as the implant magnetic arrangement 703 with opposite magnetic polarity, or it may have a conventional cylindrical shape with a magnetic field parallel to a central cylindrical axis, or it may have a spherical shape as is also known in the art.

Figure 8A:
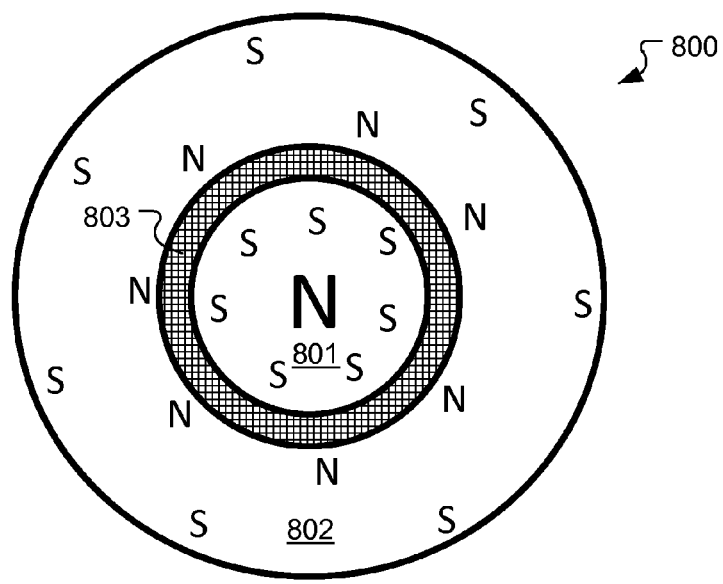
FIG. 8A-B shows an external transmitter arrangement with a magnetic yoke to interact with an implantable magnet arrangement having multiple separate magnetic segments with two-fold symmetry coupled by one or more resilient suspension elements.
Figure 8B:
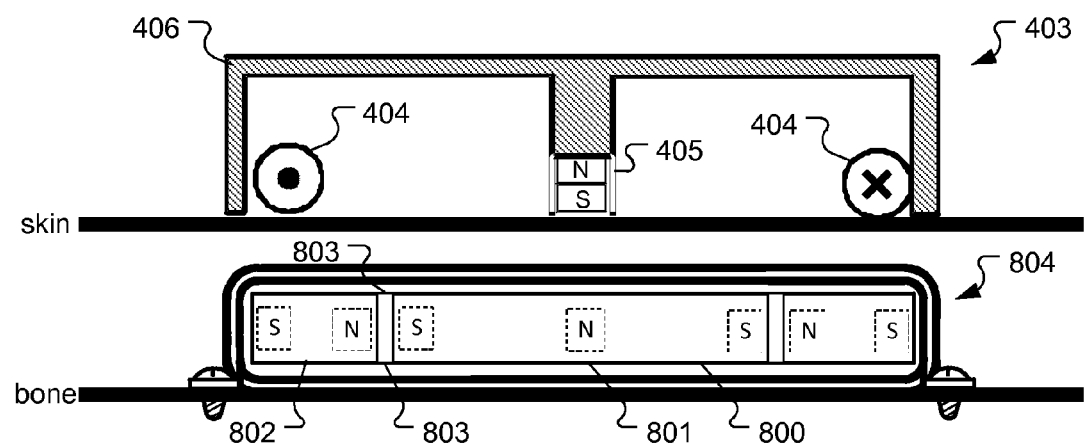

Embodiments of the present invention also are directed to an implantable transducer arrangement for a medical implant system for a patient user based on the implant magnet arrangements described above. FIG. 8A shows a top plan view and FIG. 8B shows a side cross-section view of such an implantable magnet arrangement 800 with at least two-fold magnetic symmetry, in this case, with radial symmetry. An implantable housing 804 hermetically encapsulates an interior housing volume and is fixedly attached to skull bone beneath the skin of the patient user. The magnetic transducer includes an implantable magnet arrangement 800 that is located within the housing volume and includes multiple local magnets with different independent local magnetic fields that are combined together to form a net magnetic field with at least two-fold symmetry (e.g., radial symmetry) and zero net magnetic dipole moment. The implantable magnet arrangement 800 also includes suspension elements 803 that resiliently couple adjacent local magnets to allow their relative movement. The magnetic transducer arrangement 800 forms a coupled oscillating system with the magnetic field of the drive coils 404 in an external device 403 on the skin of the patient user to develop a mechanical stimulation signal to the implantable housing 804 that is coupled to the underlying skull bone and delivered by bone conduction to the fluid within the cochlea.

In the specific embodiment shown in FIG. 8B, the magnetic transducer arrangement 800 includes a disk shaped inner local magnet 801 having a first local magnetic field as the implant magnet shown in FIG. 4, with the north magnetic pole at its radial center and the south magnetic pole distributed around its outer circumference. The magnetic transducer arrangement 800 also includes a ring shaped outer circumference local magnet 802 having a second local magnetic field. The local magnetic fields of the inner local magnet 801 and the outer circumference local magnet 802 have different directional orientations as shown, in which both local magnets 801 and 802 are MRI-safe on their own. The suspension elements 803 are in the specific form of a pair of spring membranes lying in parallel planes and coupled on one side to the inner local magnet 801 and on the opposite side to the outer circumferential local magnet 802. The inner local magnet 801 may move in accordance to the spring constant of the suspension element material and in response to the driving force induced by driving current through the drive coil 404 in the external device 403. The outer circumference local magnet 802 may be fixed to the implantable housing 804 or there may be additional suspension elements as above.

Although various exemplary embodiments of the invention have been disclosed, it should be apparent to those skilled in the art that various changes and modifications can be made which will achieve some of the advantages of the invention without departing from the true scope of the invention.

What is claimed is:

1. An implantable bone conduction transducer arrangement for a medical implant system for a patient user, the arrangement comprising: an implantable housing configured to be fixedly attached to skull bone of the patient user with an outer surface immediately under and parallel to overlying skin of the patient user; and a disk shaped transducer magnet located within the implantable housing and configured to magnetically interact with an external magnetic drive component fixedly attached on the overlying skin of the patient user to develop a mechanical bone conduction stimulation signal to the skull bone via the implantable housing, wherein the transducer magnet is characterized by a radial center surrounded by an outer circumference, and wherein the transducer magnet is characterized by:
   i. an inner local magnetic field located within the radial center and having a first magnetic pole, and
   ii. an outer local magnetic field distributed about the outer circumference and having a second magnetic pole opposite to the first magnetic pole, and wherein the inner local magnetic field and the outer local magnetic field combine together to form a net magnetic field, the net magnetic field having radial symmetry and zero net magnetic dipole moment, wherein within the arrangement itself the local magnetic fields and the net magnetic field are oriented parallel to the outer surface of the implantable housing and parallel to the overlying skin of the patient user.

* * * * *